United States Patent [19]

Cheng

[11] Patent Number: 4,850,058
[45] Date of Patent: Jul. 25, 1989

[54] PAIR OF GOGGLES AND THE MANUFACTURING METHOD THEREOF

[76] Inventor: Chensan Cheng, No. 181, Erh-Sheng 1 Rd., Chien-Chen District, Kaoshiung City, Taiwan

[21] Appl. No.: 174,510

[22] Filed: Mar. 28, 1988

[51] Int. Cl.$^4$ ............................................. A61F 9/02
[52] U.S. Cl. ............................................. 2/439; 2/448; 2/449
[58] Field of Search ............ 2/9, 410, 424–425, 2/426, 431, 439, 448–450, 454, 427, 428

[56] References Cited

U.S. PATENT DOCUMENTS

| | | | |
|---|---|---|---|
| 450,515 | 4/1891 | Lamb | 2/427 |
| 1,270,139 | 6/1918 | Fulford | 2/439 |
| 1,562,319 | 11/1925 | Fairall | 2/454 |
| 2,364,354 | 12/1944 | Felch | 2/9 X |
| 2,389,707 | 11/1945 | Wylde et al. | 2/431 |
| 2,524,245 | 10/1950 | Wold | 2/428 |
| 2,527,027 | 10/1950 | Mull | 2/450 |
| 2,589,575 | 3/1952 | Richardson et al. | 2/454 |
| 2,799,020 | 7/1957 | Currie | 2/428 X |
| 2,907,041 | 10/1959 | Finn | 2/454 X |
| 3,186,005 | 6/1965 | Geatile | 2/427 X |
| 3,330,051 | 7/1967 | Pambello | 2/454 X |
| 3,614,216 | 10/1971 | Rosenthal | 2/454 X |
| 3,705,760 | 12/1972 | Langendorfer et al. | 2/427 X |
| 3,791,722 | 2/1974 | Ahlberg et al. | 2/427 X |
| 4,122,847 | 10/1978 | Craig | 2/15 X |

FOREIGN PATENT DOCUMENTS

| | | | |
|---|---|---|---|
| 363594 | 12/1931 | United Kingdom | 2/454 |
| 579754 | 8/1946 | United Kingdom | 2/450 |
| 608059 | 9/1948 | United Kingdom | 2/450 |

OTHER PUBLICATIONS

German Publication #3030451 A1, Date of Publication 2/25/82, Applicant: Müller, Country: Germany.
Gershman, Maurice, *The Journal of the AMA*, "Self Adhering Nylon Tapes".

Primary Examiner—Werner H. Schroeder
Assistant Examiner—Jeanette E. Chapman
Attorney, Agent, or Firm—Cushman, Darby & Cushman

[57] ABSTRACT

A pair of goggles includes a transparent goggle body of flexible sheet material which may be worn on the head of a person. The goggle body is unitary and has a front shield, an upper shield extending rearwardly from the upper edge of the front shield, and a pair of opposed side shields respectively extending rearwardly from two opposite side edges of the front shield and coupled with the upper shield. The manufacturing method of the goggle body includes the steps of (1) pressing and shearing a large sheet material into a small sheet material of a predetermined outline which has a front shield area, an upper shield area, and two side shield areas; and (2) folding the upper and side shield areas rearwardly relative to the front shield area to form the front, upper, and side shields, and subsequently coupling the side shields with the upper shield to form the goggle body.

10 Claims, 7 Drawing Sheets

1

PAIR OF GOGGLES AND THE MANUFACTURING METHOD THEREOF

BACKGROUND OF THE INVENTION

This invention relates to a pair of goggles, and more particularly to a pair of inexpensive, lightweight goggles which is easily manufactured and transported.

A pair of goggles is used to protect the eyes of a wearer from water, light, dust, cold, bacteria, etc. Referring to FIG. 1, a pair of conventional goggles G typically has a unitary shield 10 of soft material, a glass 11 fixed at the front end of the shield 10, and a cord 12 fastened to two sides of the shield 10 at its ends. Because the goggles G are expensive and durable, They suffer from the following disadvantages:

1. After the goggles G have been used, it is difficult to clean and sterilize the same.
2. If the goggles G are used for a long time, the wear of the glass 11 is inevitable.
3. The goggles G weigh about 70–100 g, making the wearer uncomfortable.

SUMMARY OF THE INVENTION

It is therefore an object of this invention to provide a pair of inexpensive goggles of disposable style which may be thrown away after it has been used.

It is another object of this invention to provide a pair of goggles which is easily manufactured and transported, lowering its manufacturing and transportation costs.

It is still another object of this invention to provide a pair of lightweight goggles which can be comfortably worn on the head of a person.

It is therefore the main feature of this invention to provide a pair of goggles with a unitary goggle body of flexible, transparent sheet material which is used as a substitute for the shield and glass unit of the aforementioned conventional goggles.

According to an aspect of this invention, a pair of goggles includes a transparent goggle body of flexible sheet material and means for wearing the goggle body on the head of a person. The goggle body has a front shield, an upper shield extending rearwardly from the upper edge of the front shield, and a pair of opposed side shields respectively extending rearwardly from two opposite side edges of the front shield and coupled with the upper shield.

According to another aspect of this invention, a method for manufacturing a pair of goggles is provided. The pair of goggles includes a transparent goggle body and means for wearing the goggle body on the head of a person. The goggle body is made of a flexible sheet material and has a front shield, an upper shield extending rearwardly from the upper edge of the front shield, and a pair of opposed side shields respectively extending rearwardly from two opposite side edges of the front shield and coupled with the upper shield. The manufacturing method includes the steps of: (1) pressing and shearing a large sheet material into a small sheet material of a predetermined outline which has a front shield area, an upper shield area, and two side shield areas; (2) folding the upper and side shield areas rearwardly relative to the front shield area to form the front, upper, and side shields, and subsequently coupling the side shields with the upper shield to form the goggle body; and (3) mounting the wearing means on the side shields.

BRIEF DESCRIPTION OF THE DRAWINGS

Other features and advantages of this invention will become apparent in the following detailed description of the preferred embodiments of this invention with reference to the accompanying drawings in which.

DETAILED DESCRIPTION OF THE PREFERRED EMBODIMENTS

Figure 1:
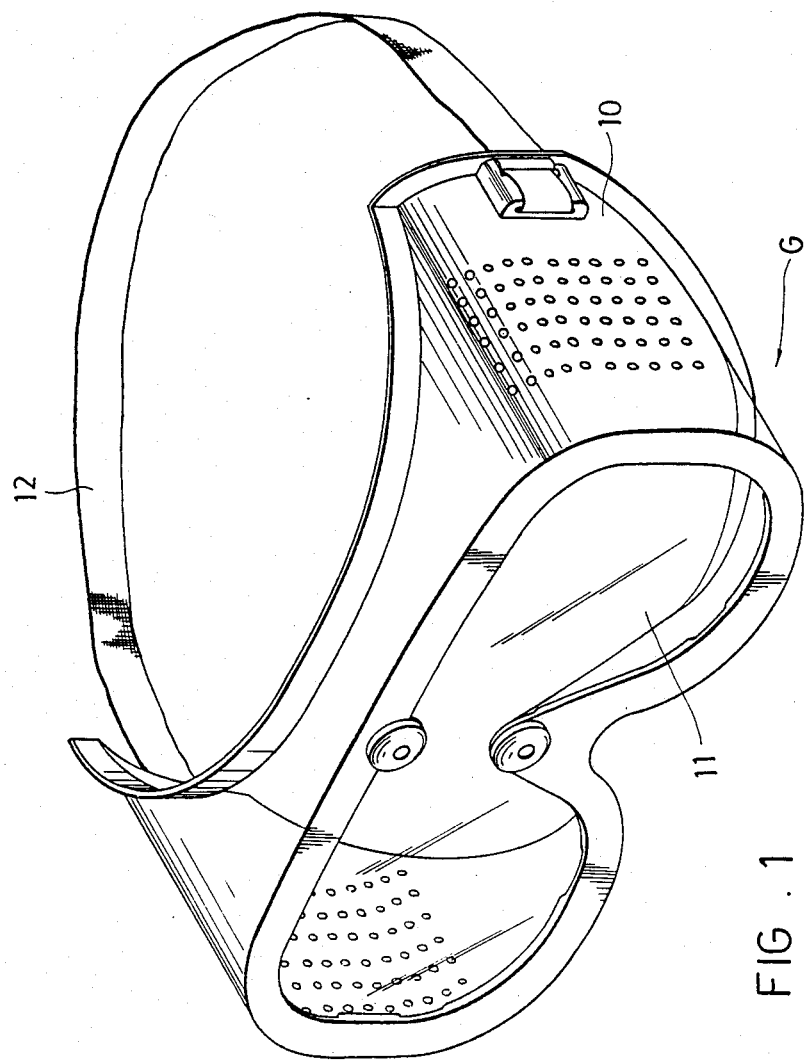
FIG. 1 is a perspective view of a pair of conventional goggles.
Figure 2:
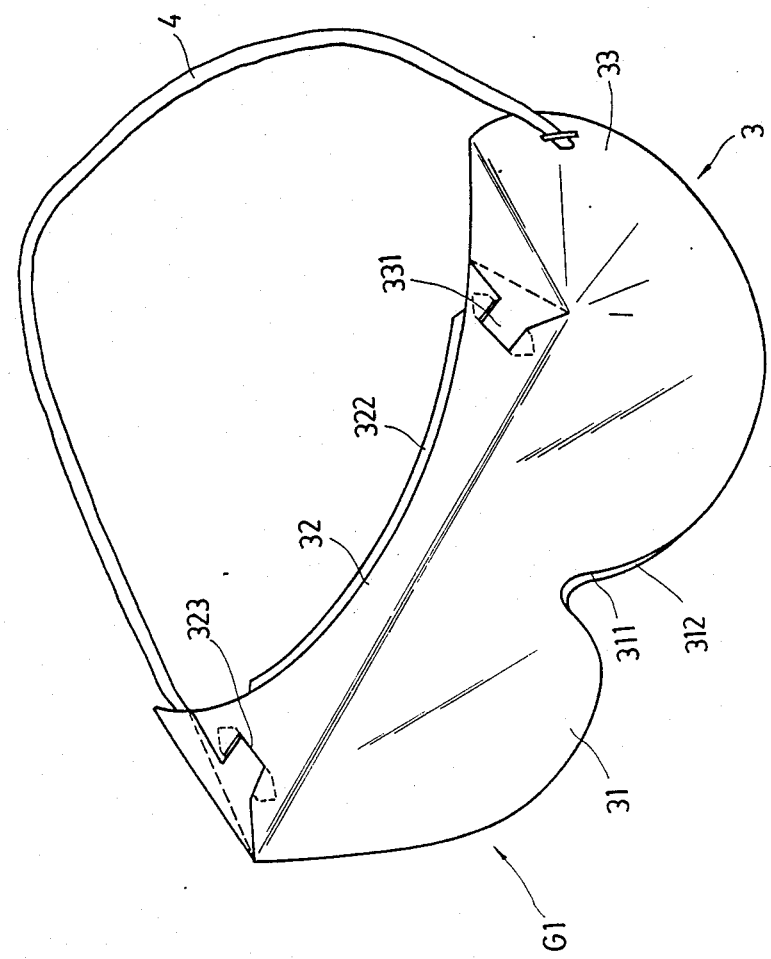
FIG. 2 is a perspective view of a pair of goggles according to a first embodiment of this invention.

Referring to FIG. 2, a pair of goggles G1 according to a first embodiment of this invention includes a unitary goggle body 3 and a cord 4 connected to the goggle body 3. The goggle body 3 is made of a flexible, transparent sheet material, such as a sheet of cellulose acetate, and has a front shield 31, an upper shield 32 extending rearwardly from the upper edge of the front shield 31, and two side shields 33 extending rearwardly from two side edges of the front shield 31. The front shield 31 is formed at the middle portion of the lower edge thereof with a concaved edge 311 from which a nose abutment strip 312 extends rearwardly for abutting snugly against the nose of the wearer. The upper shield 32 has a curved rear edge 321 from which a forehead abutment strip 322 extends downwardly for abutting snugly against the forehead of the wearer. Each of the side shields 33 is formed at its upper edge with a hook 331 which is inserted into two adjacent slits 323 in the upper shield 32 for coupling the upper shield 32 with the side shields 33. The cord 4 is fastened to the side shields 33 at its two ends so as to sleeve the goggles G1 on the head of the wearer.

Figure 3:
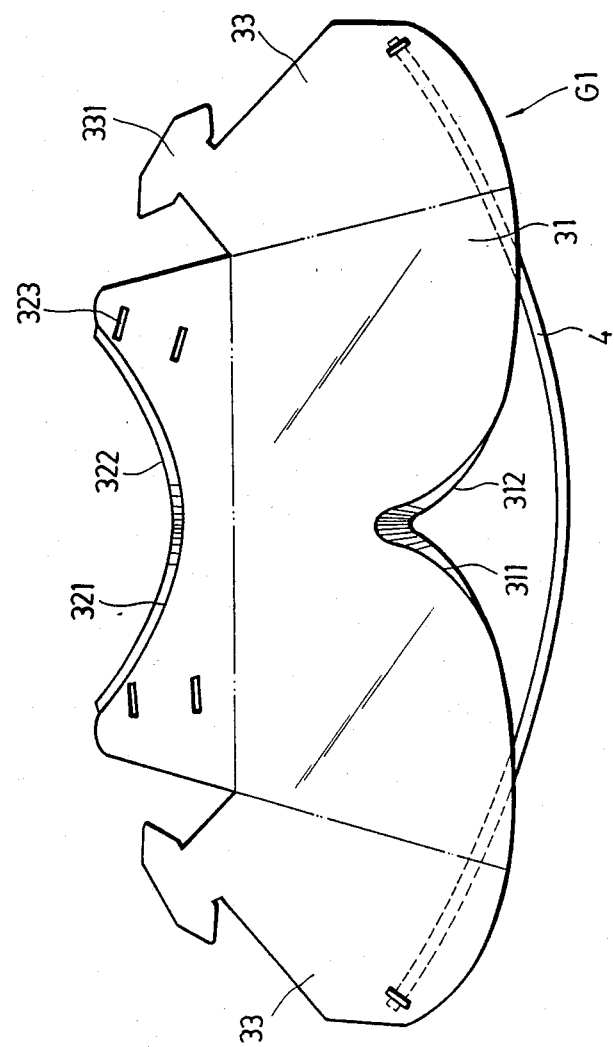
FIG. 3 is a schematic view illustrating the goggles according to the first embodiment of this invention in which the goggle body is unfolded.

The goggle body 3 is folded from a sheet material of a predetermined outline shown in FIG. 3 which has the areas of the front shield 31, upper shield 32, and side shields 33. The sheet material is pressed and shorn from a large sheet of cellulose acetate.

Figure 4:
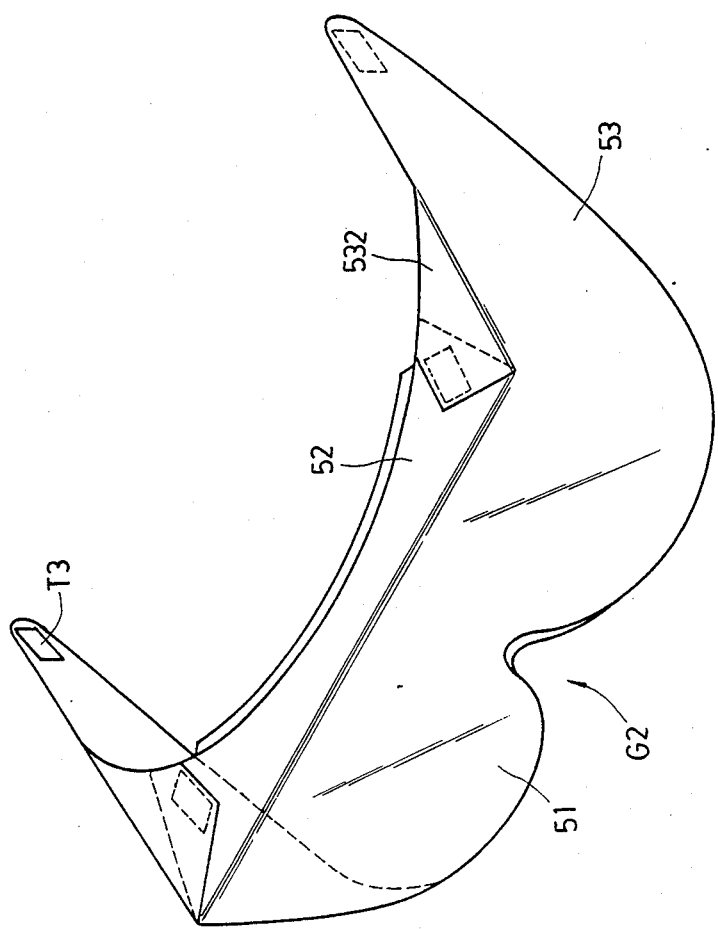
FIG. 4 is a perspective view of a pair of goggles according to a second embodiment of this invention.
Figure 5:
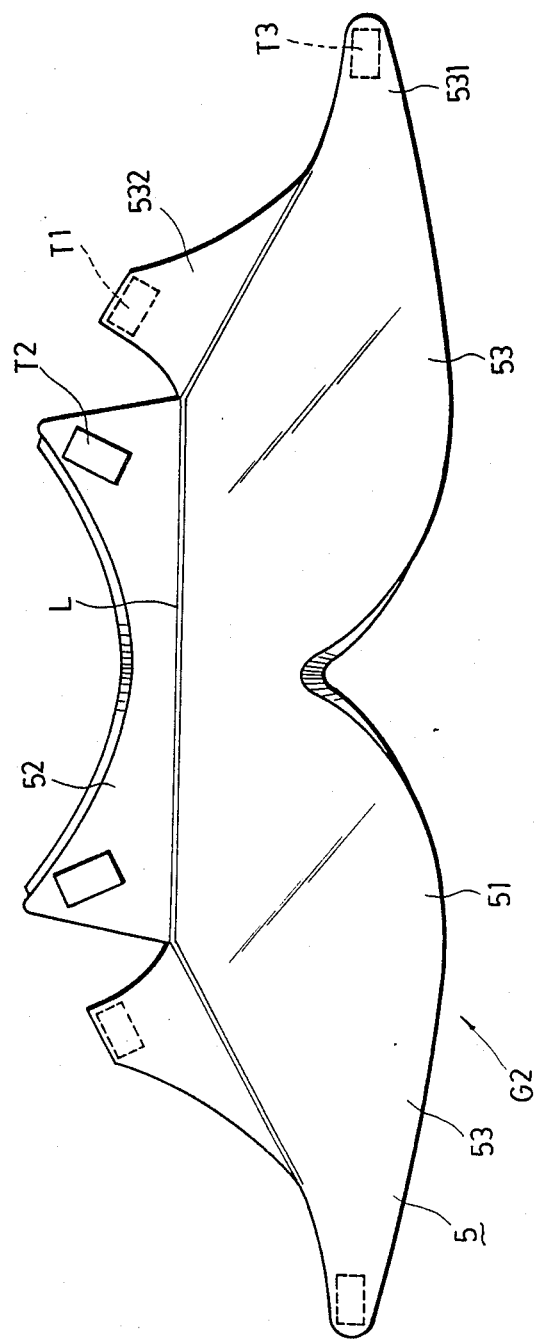
FIG. 5 is a schematic view illustrating the goggles according to the second embodiment of this invention in which the goggle body is unfolded.
Figure 6:
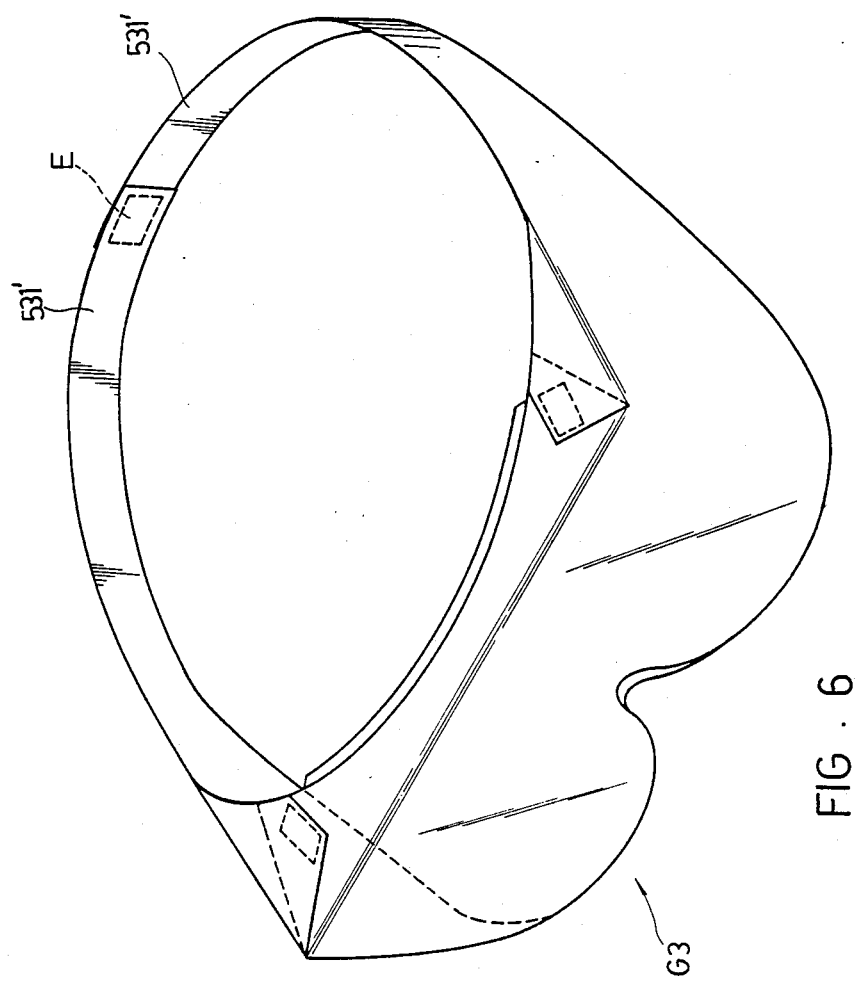
FIG. 6 is a perspective view of a pair of goggles according to a third embodiment of this invention.
Figure 7:
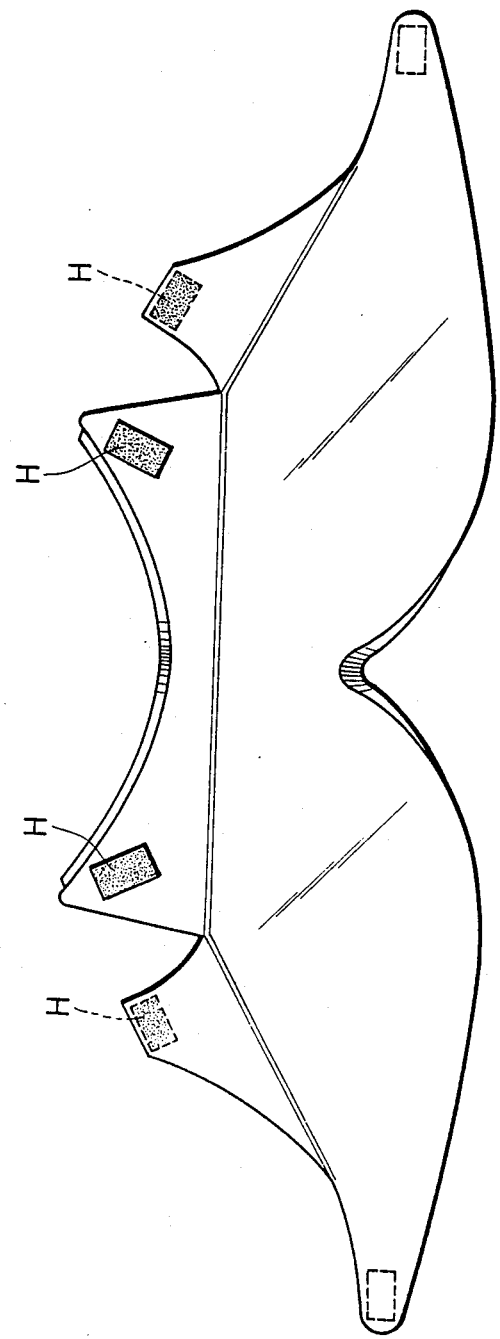
FIG. 7 is a schematic view illustrating a pair of goggles according to a fourth embodiment of this invention in which the goggle body is unfolded.

Referring to FIGS. 4 and 5, a pair of goggles G2 according to a second embodiment of this invention is shown. The goggles G2 also has a unitary goggle body 5 which has a front shield 51, an upper shield 52, and two side shields 53. The goggle body 5 is formed between the front shield 51 and the upper shield 52 with a folding line L along which the goggle body 5 is thinner than the remaining parts thereof. Each of the side shields 53 has an extended rear end portion 531 and an extended upper end portion 532 which is defined by the extension of the folding line L. When the upper shield 52 and the extended upper end portion 532 of one side shield 53 are folded along said folding line L to abut each other, a first adhesive tape T1 secured to the extended upper end portion 532 of the side shield 53 is engaged with a second adhesive tape T2 secured to the upper shield 52, so that the side shield 53 can be fixed vertically relative to the upper shield 52. The extended rear end portions 531 of the side shields 53 include third adhesive taps T3 which may be adhered to the cheeks of a wearer. Alternatively, the side shields may be further extended rearwardly to couple with each other so as to construct the goggles G3 of FIG. 6. The elongated side shields 531' of the goggles G3 are provided with engagement elements E, such as adhesive tape or hook-and-loop bands, so as to couple with each other. It is understood that the first and second adhesive tapes T1 and T2 may be replaced with other engagement elements, such as hook-and-loop bands (see FIG. 7). Certainly, folding lines may be formed between the front shield and each of the side shields.

Optionally, protective membranes may be attached removably to both faces of the front shield in a known manner.

The advantages of the goggles according to this invention are as follows:

(1) Because the goggles of this invention weigh only about 5-6 g, they can be worn comfortably on the head of a person.

(2) Because the goggles of this invention have a simple structure and are easy to manufacture and assemble, the manufacturing costs are so low that the goggles may be thrown away after they have been used.

(3) Because the goggle body of this invention can be unfolded into a flat sheet material, its transport and storage costs are reduced.

With this invention thus explained, it is apparent that numerous modifications and variations can be made without departing from the scope and spirit of this invention. For example, the side shields may be welded to two opposed side portions of the upper shield. It is therefore intended that this invention be limited only as indicated in the appended claims.

I claim:

1. A pair of goggles comprising:
a transparent goggle body of flexible sheet material having a front shield, an upper shield extending rearwardly from an upper edge of said front shield, a pair of opposed side shields respectively extending rearwardly from two opposite side edges of said front shield, and means for coupling including one of said upper shields and said side shields having a slit therein, the other of said upper shields and said side shields including a hook extending therefrom, said hook being inserted into said slit for coupling said upper shield with said side shield, said goggle body being a unitary member which is prepressed to form three straight folding lines whereby said goggle body is divided into a front shield area, an upper shield area, and two side shield areas, one of said folding lines being positioned between said front and upper shield areas, the other two of said folding lines being positioned between said front and side shield areas, respectively,; so that said goggle body can be folded into said front shield, said upper shield, and said side shields, thereby defining a space between said front shield and eyes of a person when said goggles are worn, and
means for wearing said goggle body on the head of a person.

2. A pair of goggles as claimed in claim 1, wherein said upper shield has a curved rear edge for abutting snugly against forehead of said person.

3. A pair of goggles as claimed in claim 2, wherein said upper shield is integrally formed with a forehead abutment strip extending downwardly from said curved rear edge thereof, said forehead abutment strip being adapted to abut against said forehead of said person.

4. A pair of goggles as claimed in claim 1, wherein said front shield is formed at a middle portion of lower edge thereof with a concaved edge for abutting snugly against nose of said person.

5. A pair of goggles as claimed in claim 4, wherein said front shield is integrally formed with a nose abutment strip extending rearwardly from said concaved edge thereof, said nose abutment strip being adapted to abut against said nose of said person.

6. A pair of goggles as claimed in claim 1, wherein said wearing means includes a cord having two ends which are fastened to said respective side shields.

7. A method for manufacturing a pair of goggles, said pair of goggles including a transparent goggle body and means for wearing said goggle body on the head of a person, said goggle body being made of a flexible sheet material and having a front shield, an upper shield extending rearwardly from an upper edge of said front shield, and a pair of opposed side shields respectively extending rearwardly from two opposite side edges of said front shield and coupled to said upper shield, said method comprising:

(1) pressing and shearing a large sheet material into a small sheet material of a predetermined outline in such a manner that said small sheet material is pressed to form three straight folding lines whereby said small sheet material is dividing into a front shield area, an upper shield area, and two side shield areas, one of said folding lines being positioned between said front and upper shield areas, another two of said folding lines be positioned between said front and side shield areas;

(2) folding said upper and side shield areas rearwardly relative to said front shield area to form said front, upper and side shields, and subsequently coupling said side shields to said upper shield to form said goggle body; and (3) mounting said wearing means on said side shields.

8. A method for manufacturing a pair of goggles, said pair of goggles including a transparent goggle body and means for wearing said goggle body on head of a person, said goggle body being made of a flexible sheet material and having a front shield, an upper shield extending rearwardly from an upper edge of said front shield and having two opposed slits in its opposite side portions, and a pair of opposed side shields respectively extending rearwardly from two opposite side edges of said front shield, each of said side shields having a hook extending therefrom so that said hook is inserted into said corresponding slit in said upper shield, thereby coupling with said upper shield, said method comprising the steps of:

(1) pressing and shearing a large sheet material into a small sheet material of a predetermined outline which has a front shield area, an upper shield area, and two side shield areas each having a hook area;

(2) forming said slits in said upper shield area;

(3) folding said upper and side shield areas rearwardly relative to said front shield area to form said front shield, said upper shield, and said side shields each having said hook, and subsequently inserting said hooks of said side shields into said slits in said upper shield to form said goggle body; and (4) mounting said wearing means on said side shields.

9. A method for manufacturing a pair of goggles, said pair of goggles including a transparent goggle body and means for wearing said goggle body on head of a person, said goggle body being made of a flexible sheet material and having a front shield, an upper shield extending rearwardly from an upper edge of said front shield and including two opposed first engagement elements secured to two opposite side portions of said upper shield, a pair of opposed side shields respectively extending rearwardly from two opposite side edges of said front shield, each of said side shields including a second engagement element secured thereto for engaging with said corresponding first engagement element of said upper shield, said method comprising the steps of:

(1) pressing and shearing a large sheet material into a small sheet material of a predetermined outline which has a front shield area, an upper shield area, and two side shield areas;

(2) attaching said first engagement elements to said upper shield area while attaching said second engagement elements to said side shield areas respectively;

(3) folding said upper and side shield areas rearwardly relative to said front shield area to form said front, upper, and side shields, and subsequently engaging said second engagement elements of said side shields with said first engagement elements of said upper shield to form said goggle body; and (4) mounting said wearing means on said side shields.

10. A method as claimed in claim 9, wherein said step (1) includes a sub-step of pressing said small sheet material to form a folding line between said front shield area and said upper shield area, said small sheet material being thinner along said folding line than at remaining parts thereof.

* * * * *